(12) United States Patent
Singer et al.

(10) Patent No.: US 6,936,554 B1
(45) Date of Patent: Aug. 30, 2005

(54) NONWOVEN FABRIC LAMINATE WITH MELTBLOWN WEB HAVING A GRADIENT FIBER SIZE STRUCTURE

(75) Inventors: Irwin J. Singer, Lawrenceville, GA (US); Bryan David Haynes, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 758 days.

(21) Appl. No.: 09/724,622

(22) Filed: Nov. 28, 2000

(51) Int. Cl.[7] .............................. D04H 5/00; D04H 1/56
(52) U.S. Cl. ...................... 442/327; 442/400; 442/382; 442/381; 442/401
(58) Field of Search ................................ 442/327, 381, 442/400

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,458,387 A | 7/1969 | Suskind et al. | 161/154 |
| 3,502,538 A | 3/1970 | Petersen | 161/150 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 4,196,245 A | 4/1980 | Kitson et al. | 428/198 |
| 4,340,563 A | 7/1982 | Appel et al. | 264/518 |
| 4,714,647 A | 12/1987 | Shipp, Jr. et al. | 428/212 |
| 4,756,786 A | 7/1988 | Malaney | 156/308.2 |
| 4,904,521 A | 2/1990 | Johnson et al. | 428/284 |
| 5,073,436 A | 12/1991 | Antonacci et al. | 428/219 |
| 5,213,881 A | 5/1993 | Timmons et al. | 428/224 |
| 5,258,220 A | 11/1993 | Joseph | 428/284 |
| 5,415,925 A | 5/1995 | Austin et al. | 428/287 |
| 5,454,848 A | 10/1995 | Miller | 65/442 |
| 5,464,688 A | 11/1995 | Timmons et al. | 428/298 |
| 5,492,751 A | 2/1996 | Butt, Sr. et al. | 428/198 |
| 5,554,435 A | 9/1996 | Gupta et al. | 428/224 |
| 5,616,408 A | 4/1997 | Oleszczuk et al. | 442/346 |
| 5,660,910 A | 8/1997 | Hoyt et al. | 428/95 |
| 5,679,042 A | 10/1997 | Varona | 442/347 |
| 5,804,512 A | 9/1998 | Lickfield et al. | 442/346 |
| 5,811,178 A | 9/1998 | Adam et al. | 428/218 |
| 5,817,584 A | 10/1998 | Singer et al. | 442/345 |
| 5,855,784 A | 1/1999 | Pike et al. | 210/505 |
| 5,885,909 A | 3/1999 | Rudisill et al. | 442/82 |
| 5,939,341 A | 8/1999 | Brown et al. | 442/351 |
| 6,001,303 A | 12/1999 | Haynes et al. | 264/555 |

FOREIGN PATENT DOCUMENTS

| | | | | |
|---|---|---|---|---|
| EP | 0 399 495 A1 | 11/1990 | | D04H 1/56 |
| EP | 0 729 375 B1 | 4/1999 | | B01D 39/08 |
| WO | WO 00/37723 | 6/2000 | | |
| WO | WO 01/00917 A1 | 1/2001 | | D01F 6/46 |

Primary Examiner—Glenn Caldarola
Assistant Examiner—Alexis Wachtel
(74) Attorney, Agent, or Firm—Pauley Petersen & Erickson

(57) ABSTRACT

A nonwoven fabric laminate having a meltblown layer positioned between two spunbond nonwoven layers. The meltblown layer having a gradient fiber size structure across a thickness thereof with at least one layer of coarse meltblown fibers. In one embodiment, the gradient fiber size structure has at least two layers of meltblown fibers, for example at least one layer of fine meltblown fibers and at least one layer of coarse meltblown fibers, having a mean fiber diameter difference of at least 4.0 microns.

21 Claims, 3 Drawing Sheets

NONWOVEN FABRIC LAMINATE WITH MELTBLOWN WEB HAVING A GRADIENT FIBER SIZE STRUCTURE

BACKGROUND OF THE INVENTION

Nonwoven fabric laminates are useful for a wide variety of applications. Such nonwoven fabric laminates are useful for wipers, towels, industrial garments, medical garments, medical drapes and similar articles. Disposable fabric laminates are used in hospital operating rooms for drapes, gowns, towels, footcovers, sterile wraps and the like. These surgical fabric laminates are generally spunbond/meltblown/spunbond (SMS) laminates having nonwoven outer layers of spunbond polypropylene and an inner layer of meltblown polypropylene. The outer spunbond layers provide strength and durability to the SMS laminate. The inner meltblown layer inhibits the flow or strikethrough of fluids through the SMS laminate yet allows for breathability.

However, there remains a need for a meltblown layer for use in the SMS laminate which provides an "open" structure with high breathability and a "closed" structure with desired barrier properties, high opacity and/or better coverage.

SUMMARY OF THE INVENTION

In response to the discussed difficulties and problems encountered in the prior art, a fabric laminate having a meltblown web with a gradient fiber size structure disposed between two nonwoven layers, has been discovered. Desirably, each nonwoven layer is a spunbond nonwoven layer of substantially continuous fibers. The meltblown web includes at least one layer of coarse meltblown fibers and may include at least one layer of fine meltblown fibers, which form the gradient fiber size structure across a thickness of the meltblown layer.

The SMS fabric laminate of this invention has good strength, flexibility and drape and may be formed into various articles or garments such as surgical gowns, surgical drapes and the like. The barrier properties of the SMS fabric laminate make it particularly suitable for medical applications, such as surgical gowns, but the SMS fabric laminate is also useful for any other application where barrier properties are desirable.

The nonwoven spunbond layers are produced using conventional spunbonding processes and have substantially continuous thermoplastic spunbond fibers. In accordance with one embodiment of this invention, the meltblown web has at least two layers of meltblown fibers, with at least one of the layers of meltblown fibers having a plurality of coarse meltblown fibers, which provide the desired breathability to the meltblown web. The meltblown web may also include at least one layer of fine meltblown fibers, which provide the desired barrier properties to the meltblown web.

Particularly desirable meltblown fibers for the layers of the meltblown web include monocomponent fibers, for example polypropylene fibers. In addition to polypropylene fibers, the present invention can be carried out using any thermoplastic polymer resin that can be meltblown to form a meltblown web. In one embodiment of this invention, the layers of the meltblown web may include bicomponent fibers.

The meltblown web according to one embodiment of this invention may be formed by bonding at least two independently formed meltblown layers together. The meltblown layers are bonded surface-to-surface using conventional bonding means. The meltblown web is then bonded between the two nonwoven spunbond layers to produce the SMS fabric laminate.

The gradient fiber size structure and other physical properties of the meltblown web can be adjusted by manipulation of the various process parameters of the meltblowing process. The following parameters may be adjusted and/or varied in order to change the physical properties or characteristics of the resulting meltblown web: polymer meltflow rate; polymer melt temperature (° F.); forming height (inches); primary air pressure (psi); and vacuum under forming belt or underwire vacuum (inches of water).

Alternatively, the meltblown web layers may be formed in-line with the SMS fabric laminate. In this embodiment, the SMS fabric laminate is produced using a forming apparatus having at least three stations, a spunbonding station, a meltblowing station, and a second spunbonding station. Desirably, a plurality of meltblowing stations are utilized to form a meltblown web having at least two layers of meltblown fibers, for example at least one layer of coarse meltblown fibers and at least one layer of fine meltblown fibers, which form a gradient fiber size structure. A meltblown web including at least two layers is deposited directly on the first nonwoven spunbond layer during the in-line process. A second nonwoven spunbond layer is subsequently deposited directly on an opposite side of the meltblown web to produce the SMS fabric laminate.

With the foregoing in mind, it is a feature and advantage of the invention to provide a meltblown web for use in a SMS fabric laminate having a gradient fiber size structure across a thickness thereof.

It is also a feature and advantage of the invention to provide a SMS fabric laminate having high breathability and desired barrier properties, including high opacity and coverage.

DEFINITIONS

Figure 1:
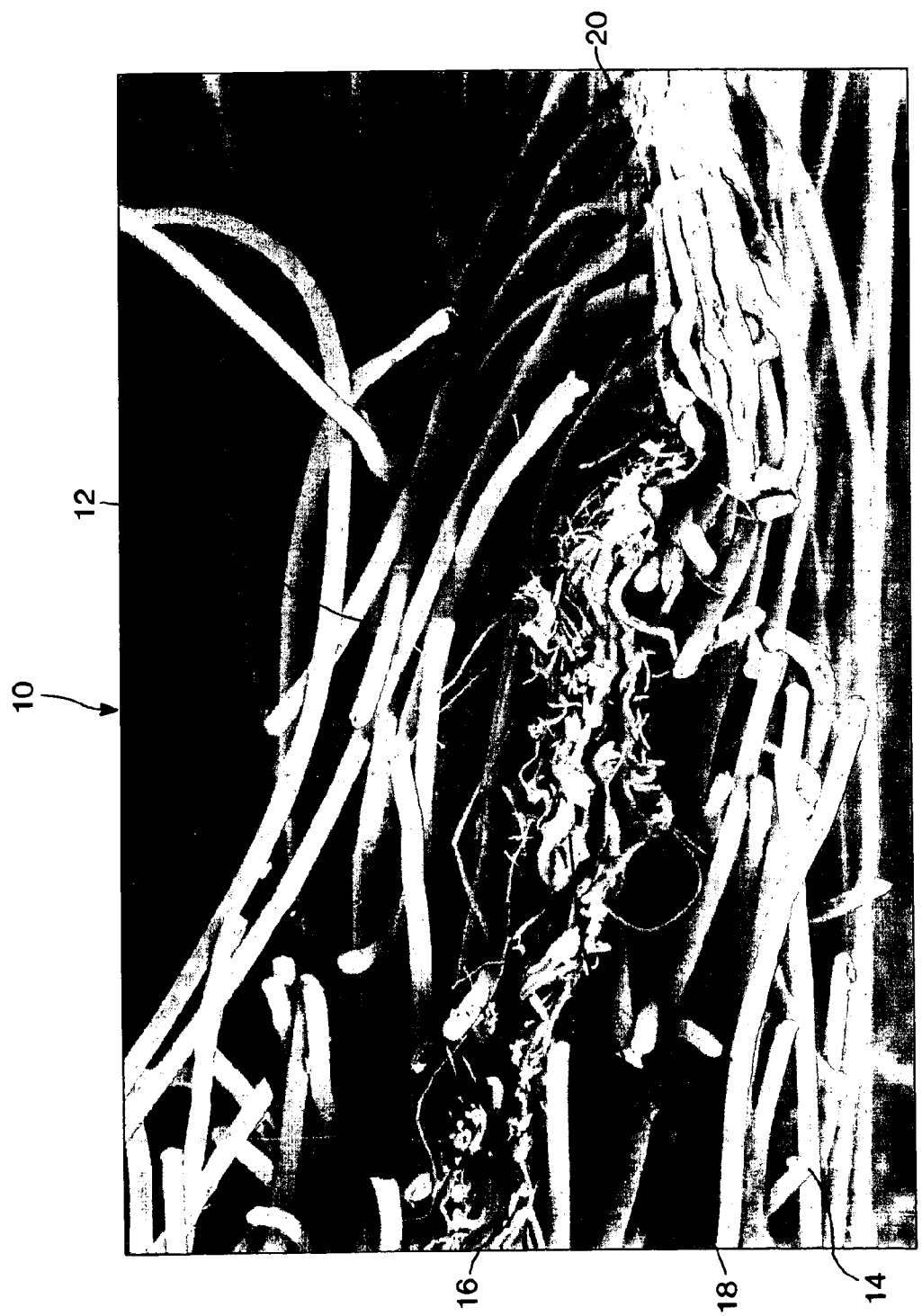
FIG. 1 shows a Scanning Electronmicrograph (SEM) image of a cross-section of a SMS fabric laminate having a meltblown web of coarse and fine fibers, in accordance with one embodiment of this invention.

As used herein, the term "coarse meltblown fibers" refers to meltblown fibers produced by a meltblowing process having an average diameter of at least about 5.0 microns, desirably about 5.0 microns to about 30 microns. A coarse fiber meltblown web has an "open" web structure.

As used herein, the term "fine meltblown fibers" refers to meltblown fibers produced by a meltblowing process having an average diameter less than about 5.0 microns, desirably about 0.1 micron to about 4.0 microns. A fine fiber meltblown web has a "closed" web structure.

The term "layer" when used in the singular refers to a layer of a multilayer web or fabric structure.

The term "meltblown fibers" means fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin and in U.S. Pat. No. 6,001,303 to Haynes, et al. Meltblown fibers are microfibers which may be continuous or discontinuous and are generally self bonding when deposited onto a collecting surface.

The term "monocomponent fiber" refers to a fiber formed from one or more extruders using only one polymer. This is not meant to exclude fibers formed from one polymer to which small amounts of additives have been added for color, anti-static properties, lubrication, hydrophilicity, etc. These additives, e.g., titanium dioxide for color, are generally present in an amount less than 5 weight percent and more typically about 2 weight percent.

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.) The terms include nonwoven fabrics or webs having multiple layers.

The term "polymer" includes, but is not limited to, homopolymers, copolymers, such as for example, block, graft, random and alternating copolymers, terpolymers, etc. and blends and modifications thereof. Further, unless otherwise specifically limited, the term "polymer" shall include all possible geometrical configurations of the material. These configurations include, but are not limited to isotactic, syndiotactic and atactic symmetries.

The term "spunbond fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average diameters larger than about 7 microns, more particularly, between about 10 and 30 microns.

These terms may be defined with additional language in the remaining portions of the specification.

DETAILED DESCRIPTION OF THE PRESENTLY PREFERRED EMBODIMENTS

As shown in FIG. 1, a SMS fabric laminate 10, in accordance with one embodiment of this invention, includes a first spunbond nonwoven layer 12, a second spunbond nonwoven layer 14 and a meltblown web 16 disposed between the first spunbond nonwoven layer 12 and the second spunbond nonwoven layer 14. In accordance with one embodiment of this invention, the meltblown web 16 has at least one layer of coarse meltblown fibers 18 and may have at least one layer of fine meltblown fibers 20, which form a gradient fiber size structure across a thickness of the meltblown web 16. Although reference is made throughout this specification and in the claims to a SMS fabric laminate, it is apparent to one skilled in the art that the meltblown web 16 may be disposed between suitable nonwoven layers which are not spunbond nonwoven layers.

Desirably, the gradient fiber size structure is formed having adjacent layers of meltblown fibers with a mean fiber diameter difference of at least 4.0 microns. For example, a layer of fine meltblown fibers 20 having a mean fiber diameter of about 2.0 microns is bonded to a layer of course meltblown fibers 18 having a mean fiber diameter of about 14.5 microns to form the meltblown web 16. Desirably, the overall basis weight of the SMS fabric laminate 10 is about 16 grams per square meter (gsm) to about 275 gsm, more desirably about 33 gsm to about 136 gsm, still more desirably about 33 gsm to about 68 gsm.

The SMS fabric laminate 10 of this invention has good strength, flexibility and drape and may be formed into various articles or garments such as surgical gowns, surgical drapes and the like. The barrier properties of the SMS fabric laminate 10 make it particularly suitable for medical applications, such as surgical gowns, but the SMS fabric laminate 10 is also useful for any other application where barrier properties are desirable.

The first nonwoven spunbond layer 12 and the second nonwoven spunbond layer 14 may be produced using spunbonding processes well known to those having ordinary skill in the art and have substantially continuous thermoplastic spunbond fibers. Desirably, the first nonwoven spunbond layer 12 and the second nonwoven spunbond layer 14 each has a basis weight of about 10 grams per square meter (gsm) to about 100 gsm, more desirably about 12 gsm to about 24 gsm. It is also desirable that the spunbond fibers have an average diameter of about 10 microns to about 30 microns, more desirably about 15 microns to about 25 microns.

A wide variety of thermoplastic polymers may be used to construct the the first nonwoven spunbond layer 12 and the second nonwoven spunbond layer 14 including, but not limited to polyamides, polyesters, polyolefins, copolymers of ethylene and propylene, copolymers of ethylene or propylene with a $C_4$–$C_{20}$ alpha-olefin, terpolymers of ethylene with propylene and a $C_4$–$C_{20}$ alpha-olefin, ethylene vinyl acetate copolymers, propylene vinyl acetate copolymers, styrene-poly(ethylene-alpha-olefin) elastomers, polyurethanes, A-B block copolymers where A is formed of poly (vinyl arene) moieties such as polystyrene and B is an elastomeric midblock such as a conjugated diene or lower alkene, polyethers, polyether esters, polyacrylates, ethylene alkyl acrylates, polyisobutylene, polybutadiene, isobutylene-isoprene copolymers, and combinations of any of the foregoing. Polyolefins are desirable. Polyethylene and polypropylene homopolymers and copolymers are most desirable.

Desirably, the meltblown web 16 has a basis weight of about 5 gsm to about 34 gsm, more desirably about 9 gsm to about 15 gsm. In accordance with one embodiment of this invention, the meltblown web 16 includes at least two layers of meltblown fibers 17 and 19, as shown in FIG. 1. At least one of the layers of meltblown fibers 17, 19 has a plurality of coarse meltblown fibers 18. The coarse meltblown fibers 18 have an average diameter of at least about 5.0 microns, desirably about 5.0 microns to about 30 microns. The coarse meltblown fibers 18 provide an "open" web structure, which provides the desired breathability to the meltblown web 16.

The meltblown web 16 may also have at least one layer of fine meltblown fibers 20, as shown in FIG. 1. The fine meltblown fibers 20 have an average diameter less than about 5.0 microns, desirably about 0.1 micron to about 4.0 microns. The fine meltblown fibers 20 provide a "closed" web structure, which provides the desired barrier properties, including high opacity and coverage, to the meltblown web 16.

The meltblown web 16 may be constructed of the same or similar thermoplastic polymers used to construct the first nonwoven spunbond layer 12 and the second nonwoven spunbond layer 14, as discussed above. Particularly desirable meltblown fibers for the layers of the meltblown web 16 include monocomponent fibers, for example polypropylene fibers. In addition to polypropylene fibers, the present invention can be carried out using any thermoplastic polymer resin that can be meltblown to form a meltblown web.

Figure 2:
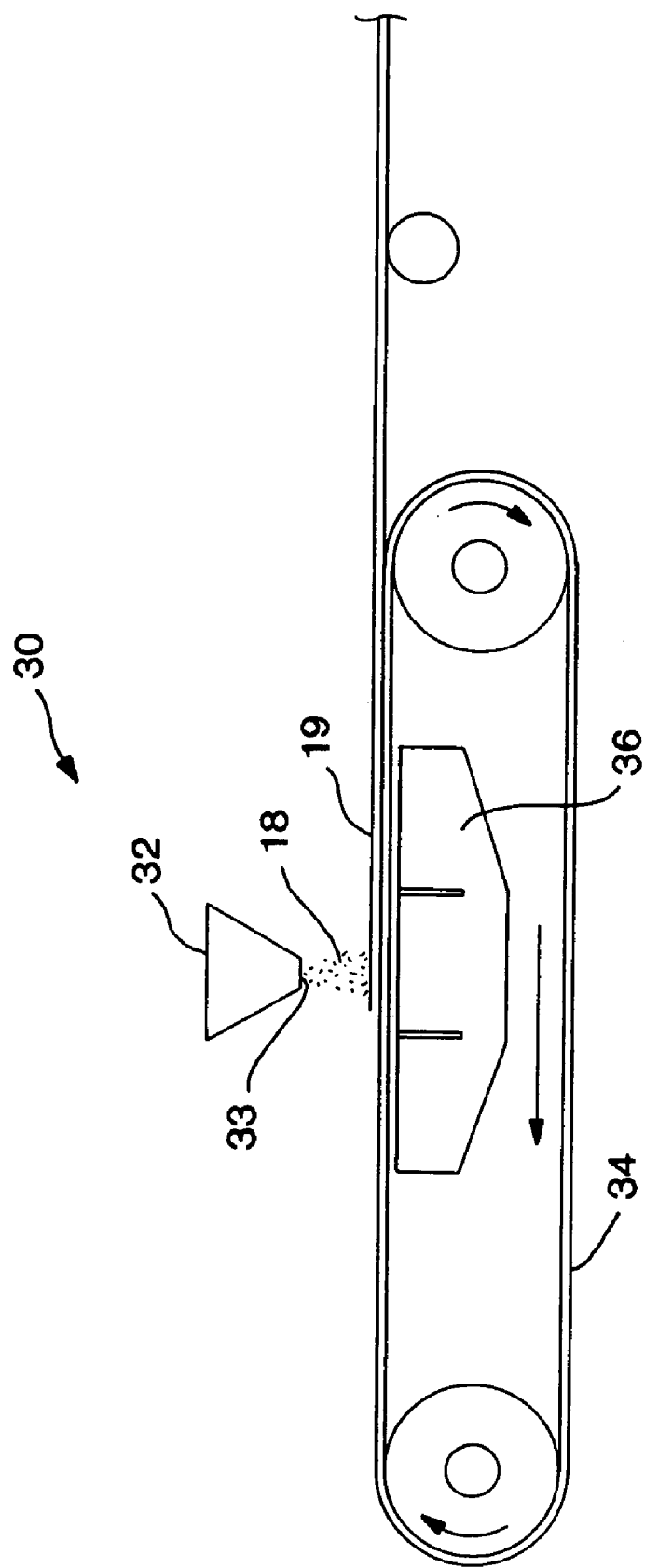
FIG. 2 is a schematic view of a forming apparatus used to produce a meltblown layer, in accordance with one embodiment of this invention.

The meltblown web 16 according to one embodiment of this invention may be formed by bonding at least two meltblown layers of meltblown fibers together. The meltblown layers are bonded surface-to-surface using conventional bonding means, including, but not limited to thermal bonding, ultrasonic bonding and adhesive bonding. In this embodiment, the meltblown layers are independently formed using a forming apparatus 30, as shown in FIG. 2, and subsequently bonded together.

The meltblown web 16 may also be formed with the first nonwoven spunbond layer 12 and the second nonwoven spunbond layer 14 as a continuous in-line process, as discussed below. The forming apparatus 30 includes a meltblown station 32 having a die 33 which is used to form meltblown fibers, for example coarse meltblown fibers 18 and fine meltblown fibers 20 (not shown). The distance between the die 33 and a forming belt 34 is designated as the "forming height." Within the meltblown station 32, a thermoplastic polymer resin, for example a polypropylene resin, is heated to a melting temperature of the thermoplastic polymer resin to form a polymer melt. As the polymer melt exits the die 33, a high pressure fluid, usually air, attenuates and spreads a stream of the polymer melt to form the coarse meltblown fibers 18. The pressure at which the air exits the die 33 is designated the "primary air pressure." The coarse meltblown fibers 18 are randomly deposited on the moving forming belt 34 to form a coarse fiber meltblown layer 19, as shown in FIG. 2.

As the coarse meltblown fibers 18 are deposited on the forming belt 34, a vacuum unit 36, positioned under the forming belt 34, draws the coarse meltblown fibers 18 towards the forming belt 34 during the formation of the coarse fiber meltblown layer 19. Desirably, the vacuum unit 36 has at least two, more desirably three independently controllable vacuum units, as shown in FIG. 2. The independently controllable vacuum units are placed along a length of the forming belt 34 to allow different vacuum settings as the coarse fiber meltblown layer 19 moves along the forming belt 34. A fine fiber meltblown web may be formed using the same or similar forming apparatus 30.

Independently formed meltblown layers are layered together or bonded together using conventional bonding techniques, for example thermal bonding and ultrasonic bonding, to form the meltblown web 16. The meltblown web 16 is then bonded between the first nonwoven spunbond layer 12 and the second nonwoven spunbond layer 14 to produce the SMS fabric laminate 10, in accordance with one embodiment of this invention.

The gradient fiber size structure and other physical properties of the meltblown web 16 can be adjusted by manipulation of the various process parameters of the meltblowing process. The following parameters may be adjusted and/or varied in order to change the physical properties or characteristics of the resulting meltblown web 16: type of polymer; polymer melt temperature (° F.); forming height (inches); primary air pressure (psi); and vacuum under forming belt or underwire vacuum (inches of water).

Figure 3:
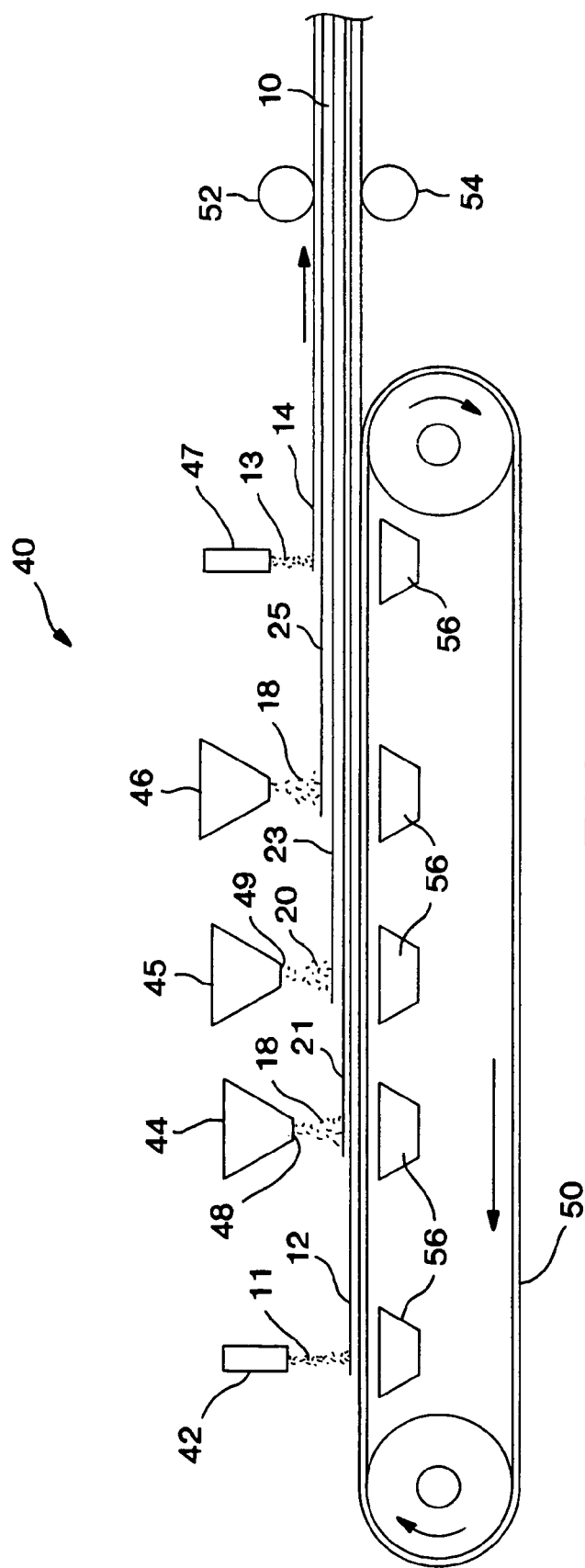
FIG. 3 is a schematic view of a forming apparatus used to produce a SMS fabric laminate having a meltblown web with a gradient fiber size structure, according to one embodiment of this invention.

As an alternative to bonding independently formed meltblown layers to form the meltblown web 16, the meltblown web 16 may be formed in-line with the SMS fabric laminate. In accordance with one embodiment of this invention, the SMS fabric laminate 10 is produced using a forming apparatus 40, as shown in FIG. 3. The forming apparatus 40 has at least three stations, a spunbonding station 42, a meltblowing station 44, and a second spunbonding station 47. Desirably, a plurality of meltblowing stations, for example meltblowing station 44, a second meltblowing station 45, and a third meltblowing station 46, are utilized to form a meltblown web 16 having a gradient fiber size structure formed by a plurality of layers of meltblown fibers.

The spunbond station 42 produces continuous spunbond fibers 11 which are deposited on a forming belt 50 to produce the first nonwoven spunbond layer 12. The spunbond station 42 and spunbond station 47 are conventional extruders with spinnerets which form the first spunbond nonwoven layer 12 and the second spunbond nonwoven layer 14, respectively, by methods well known to those having ordinary skill in the art.

The meltblowing station 44 includes a die 48 which is used to form meltblown fibers, for example coarse meltblown fibers 18. Within the meltblowing station 44, a thermoplastic polymer resin, for example a polypropylene resin, is heated to a melting temperature of the thermoplastic polymer resin to form a polymer melt. As the polymer melt exits the die 48, a high pressure fluid, usually air, attenuates and spreads a stream of the polymer melt to form the coarse meltblown fibers 18. The coarse meltblown fibers 18 are randomly deposited on the first nonwoven spunbond layer 12 moving on the forming belt 50 to form a layer 21 of coarse meltblown fibers 18.

The second meltblowing station 45 includes a die 49 which is used to form meltblown fibers, for example fine meltblown fibers 20. Within the second meltblowing station 45, a thermoplastic polymer resin, for example a polypropylene resin, is heated to a melting temperature of the thermoplastic polymer resin to form a polymer melt. As the polymer melt exits the die 49, a high pressure fluid, usually air, attenuates and spreads a stream of the polymer melt to form the fine meltblown fibers 20. The fine meltblown fibers 20 are randomly deposited on the layer 21 of coarse meltblown fibers 18 moving on the forming belt 50. The fine meltblown fibers 20 form a layer 23.

In accordance with one embodiment of this invention, the third meltblowing station 46 is aligned along the forming belt 50 to deposit meltblown fibers, for example course meltblown fibers 18, on the layer 23 to form a layer 25 of coarse meltblown fibers 18. The layers 21, 23 and 25 of meltblown fibers deposited on the first nonwoven spunbond layer 12 produce the meltblown web 16 with the gradient fiber size structure. Each meltblowing station 44, 45, 46, can be used to produce course meltblown fibers 18 or fine meltblown fibers 20, as desired.

After the meltblown web 16 is formed on the first nonwoven spunbond layer 12, the spunbond station 47 produces continuous spunbond fibers 13 which are deposited on the meltblown web 16 to produce the second nonwoven spunbond layer 14. The resulting SMS fabric laminate 10 is then fed through bonding rolls 52 and 54. The bonding rolls 52 and 54 are heated to a softening temperature of a polymer used to form at least one of the layers of the SMS fabric laminate 10. As the SMS fabric laminate 10 passes between the heated bonding rolls 52 and 54, the layers are compressed and thermally bonded together. Other conventional bonding means may be used to bond the layers of the SMS fabric laminate 10.

EXAMPLE 1

Six meltblown layers were produced using the forming apparatus shown in FIG. 2, including one fine fiber meltblown layer (designated MB Roll 01) and five coarse fiber meltblown layers (designated consecutively MB Roll 02–06). The process parameters, including the type of polymer, polymer melt temperature, forming height, primary air pressure, and/or underwire vacuum, were varied in accordance with Table 1. Desirably, the forming vacuum control is maintained at 100% output to ensure full process capacity. MB Roll 01–05 layers were produced using a medium melt flow rate polypropylene resin supplied under the trade name Montell® PF-015. MB Roll 06 layer was produced using a low melt flow rate (400 MFR) polypropylene resin, without peroxide, supplied by the Exxon Chemical Company under the trade name Exxon® 3505.

Volume-Based Mean Diameter

The volume-based mean diameter is also an average fiber diameter based on all fiber diameter measurements taken. However, the volume-based mean diameter is based on the volume of the fibers measured. The volume is calculated for each test sample and is based on a cylindrical model using the following equation:

$$V = \pi A^2 / 2P;$$

where A is the cross-sectional area of the test sample and P is the perimeter of the test sample. Fibers with a larger volume will carry a heavier weighting toward the overall average. For each test sample, 300 to 500 measurements were taken.

Anisotropy

The Anisotropy describes the orientation of the fibers. It is a dimensionless measurement and is defined by the following equation:

$$\text{Anisotropy} = \text{horizontal area/vertical intercept}.$$

It is a field measurement and is therefore measured once for each image. A value of less than 1.0 indicates a machine direction fiber orientation while a value of greater than 1.0 indicates a cross-machine direction fiber orientation. A value of 1.0 represents random fiber orientation.

TABLE 1

| MB Roll | Fiber Type | Polymer | Forming Height (inches) | Melt Temp. (° F.) | Primary Air Pressure (psi) | Underwire Vacuum 1, 2, 3 (inch of water) | Forming Vacuum Control (% Output) |
|---|---|---|---|---|---|---|---|
| 01 | Fine | PF-015 | 8 | 437 | 16 | 0, 16, 20 | 100 |
| 02 | Coarse | PF-015 | 8 | 437 | 3.8 | 0, 16, 20 | 100 |
| 03 | Coarse | PF-015 | 8 | 396 | 3.5 | 0, 16, 20 | 100 |
| 04 | Coarse | PF-015 | 10 | 402 | 4.0 | 0, 16, 20 | 100 |
| 05 | Coarse | PF-015 | 10 | 390 | 3.9 | 0, 5, 4 | 100 |
| 06 | Coarse | 3505 | 10 | 390 | 3.9 | 0, 4, 5 | 100 |

The fine fiber meltblown layer (MB Roll 01) and three coarse fiber meltblown layers (MB Roll 03, 05, and 06), produced using the forming apparatus shown in FIG. 2, were tested using an Image Analysis of Meltblown Fiber Diameter test. Each meltblown layer was tested for Count-Based Mean Diameter, Volume-Based Mean Diameter, and Anisotropy. Results of this test are displayed in Table 2. Two test samples, designated "A" and "B," were conducted for each meltblown layer.

Test Procedures

Count-Based Mean Diameter

The count-based mean diameter is the average fiber diameter based on all fiber diameter measurements taken. For each test sample, 300 to 500 fiber diameter measurements were taken.

TABLE 2

| | Count-Based Diameter | | Volume-Based Diameter | | |
|---|---|---|---|---|---|
| MB Roll | Mean (microns) | STD DEV (microns) | Mean (microns) | STD DEV (microns) | Anisotropy |
| 01A | 1.93 | 1.20 | 3.76 | 2.32 | 1.037 |
| 01B | 2.05 | 1.16 | 3.44 | 1.53 | 1.237 |
| 03A | 6.43 | 4.05 | 12.2 | 6.36 | 1.139 |
| 03B | 7.08 | 4.10 | 11.90 | 5.20 | 1.004 |
| 05A | 14.60 | 9.10 | 26.50 | 11.90 | 0.973 |
| 05B | 14.00 | 7.30 | 21.90 | 9.36 | 1.088 |
| 06A | 7.01 | 4.58 | 14.50 | 8.46 | 1.294 |
| 06B | 7.12 | 4.45 | 13.10 | 6.25 | 1.491 |

EXAMPLE 2

Selected meltblown layers from Example 1 were layered together to form five meltblown webs, as shown in Table 3. For example, a MB Roll 01 layer was layered or positioned between two MB Roll 03 layers to form one meltblown web sample. The five meltblown webs were tested for basis weight, air permeability, cup crush load, cup crush energy and opacity using standard testing procedures as outlined below. Results of these tests are displayed in Table 3.

Test Procedures

Basis Weight

The basis weight of a nonwoven fabric is determined by measuring the mass of a nonwoven fabric sample, and dividing it by the area covered by the sample. The basis weight was reported in grams per square meter (gsm).

Air Permeability

This test determines the airflow rate through a sample for a set area size and pressure. The higher the airflow rate per a given area and pressure, the more open the fabric is, thus allowing more fluid to pass through the fabric. Air permeability is determined using a pressure of 125 Pa (0.5 inch water column) and is reported in cubic feet per minute per square foot. The air permeability data reported herein can be obtained using a TEXTEST FX 3300 air permeability tester.

Cup Crush

The softness of a nonwoven fabric may be measured according to the "cup crush" test. The cup crush test evaluates fabric stiffness by measuring the peak load or "cup crush" required for a 4.5 cm diameter hemispherically shaped foot to crush a 25 cm by 25 cm piece of fabric shaped into an approximately 6.5 cm diameter by 6.5 cm tall inverted cup while the cup shaped fabric is surrounded by an approximately 6.5 cm diameter cylinder to maintain a uniform deformation of the cup shaped fabric. An average of 10 readings is used. The foot and the cup are aligned to avoid contact between the cup walls and the foot which could affect the readings. The peak load is measured while the foot is descending at a rate of 40.6 cm/minute and is measured in grams. The cup crush test also yields a value for the total energy required to crush a sample (the "cup crush energy") which is the energy from the start of the test to the peak load point, i.e. the area under the curve formed by the load in grams on one axis and the distance the foot travels in millimeters on the other. Cup crush energy is therefore reported in g-mm. Lower cup crush values indicate a softer fabric. A suitable device for measuring cup crush is a Sintech Tensile Tester and 500 g load cell using TESTWORKS Software all of which are available from Sintech, Inc. of Research Triangle Park, N.C.

Opacity

This test determines the percent opacity of a sample. The higher the opacity, the more closed the fabric is, thus providing better barrier properties, coverage and visual aesthetics. The opacity data reported herein can be obtained using a HunterLab Color Difference Meter, Model DP 9000. The sample is placed on a specimen port and a percent opacity of the sample is determined. The test is based on a percentage of light which passes through the sample. For example, when no light passes through the sample, the sample will have 100% opacity. Conversely, 0% opacity corresponds to a transparent sample.

TABLE 3

| Meltblown Layer Sample | Basis Weight (gsm) | Air Permeability (cfm) | Cup Crush Load (gm) | Cup Crush Energy (gm-mm) | Opacity (%) |
|---|---|---|---|---|---|
| MB Roll #03 MB Roll #01 MB Roll #03 | 0.42 | 176 | 21 | 243 | 51 |
| MB Roll #05 MB Roll #01 MB Roll #05 | 0.42 | 212 | 24 | 168 | 42 |
| MB Roll #01 MB Roll #06 | 0.28 | 165 | 21 | 148 | 48 |
| MB Roll #01 MB Roll #03 | 0.28 | 201 | 23 | 106 | 42 |
| MB Roll #01 MB Roll #05 | 0.28 | 227 | 17 | 109 | 39 |

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

What is claimed is:

1. A nonwoven surgical fabric laminate, comprising:
   a first nonwoven layer;
   a second nonwoven layer; and
   a meltblown web positioned between the first nonwoven layer and the second nonwoven layer, the meltblown web comprising at least one layer consisting essentially of fine meltblown fibers having a diameter less than 5.0 microns adjacent at least one layer of coarse meltblown fibers having a diameter of at least 5.0 microns, and having a gradient fiber size structure wherein the adjacent layers of the meltblown web have a mean diameter difference of at least 4.0 microns.

2. The nonwoven fabric laminate of claim 1, wherein the fine meltblown fibers have an average diameter of 0.1 micron to about 4.0 microns.

3. The nonwoven fabric laminate of claim 1, wherein the coarse meltblown fibers have an average diameter of about 6.0 microns to about 15 microns.

4. The nonwoven fabric laminate of claim 1, wherein the at least one layer of fine meltblown fibers is bonded to the at least one layer of coarse meltblown fibers.

5. The nonwoven fabric laminate of claim 4, wherein the meltblown web has an air permeability of about 176 cfm to about 227 cfm.

6. The nonwoven fabric laminate of claim 4, wherein the meltblown web has an opacity of about 39% to about 51%.

7. The nonwoven fabric laminate of claim 1, wherein the gradient fiber size structure comprises a layer of fine meltblown fibers positioned between a first layer of coarse meltblown fibers and a second layer of coarse meltblown fibers.

8. The nonwoven fabric laminate of claim 7, wherein the meltblown web has an air permeability of about 176 cfm to about 212 cfm.

9. The nonwoven fabric laminate of claim 7, wherein the meltblown web has an opacity of about 42% to about 51%.

10. The nonwoven fabric laminate of claim 1, wherein the meltblown web has a basis weight of about 5 gsm to about 34 gsm.

11. The nonwoven fabric laminate of claim 1, wherein the meltblown web has a basis weight of about 9 gsm to about 15 gsm.

12. The nonwoven fabric laminate of claim 1, wherein the first nonwoven layer and the second nonwoven layer each comprise a spunbond nonwoven layer.

13. A nonwoven surgical fabric laminate, comprising:
a first spunbond layer;
a meltblown web having a first side bonded to a first side of the first spunbond layer, the meltblown web comprising at least one layer consisting essentially of coarse meltblown fibers having a diameter less than 5.0 microns adjacent at least one layer consisting essentially of fine meltblown fibers having a diameter of at least 5.0 microns, wherein the adjacent layers of the meltblown web have a mean diameter difference of at least 4.0 microns; and
a second spunbond layer having a first side bonded to a second side of the meltblown web.

14. The nonwoven fabric laminate of claim 13, wherein the meltblown web further comprises a third layer of meltblown fibers.

15. A nonwoven surgical fibric laminate, comprising:
a meltblown web having at least one layer consisting essentially of coarse meltblown fibers adjacent at least one layer consisting essentially of fine meltblown fibers, the coarse meltblown fibers having a diameter of at least 5.0 microns and the fine meltblown fibers having a diameter of less than 5.0 microns;
the at least one layer of coarse meltblown fibers and the at least one layer of fine meltblown fibers providing a gradient fiber size structure, wherein the at least one layer of coarse meltblown fibers has a mean fiber diameter at least 4.0 microns greater than a mean fiber diameter of the at least one layer of fine meltblown fibers.

16. A medical gown comprising the laminate of claim 15.

17. A medical drape comprising the laminate of claim 15.

18. A medical garment comprising the laminate of claim 15.

19. A medical sterilization wrap comprising the laminate of claim 15.

20. A medical towel comprising the laminate of claim 15.

21. A medical foot cover comprising the laminate of claim 15.

* * * * *